US005220913A

United States Patent [19]

Horbal et al.

[11] Patent Number: 5,220,913

[45] Date of Patent: Jun. 22, 1993

[54] ELECTRODE WITH VISIBLE SPARK

[76] Inventors: Mark T. Horbal, 2 S. 530 Iroquois Ct. West, Warrenville, Ill. 60555; Christopher Nowacki, 1552 Chickamauga La., Long Grove, Ill. 60047

[21] Appl. No.: 811,745

[22] Filed: Dec. 23, 1991

[51] Int. Cl.[5] ............ A61B 17/22

[52] U.S. Cl. ............ 128/24 EL

[58] Field of Search ............ 128/24 EL, 24 A, 24.1, 128/2, 54, 4, 419 R, 421; 606/2, 127, 128; 303/141, 142, 118; 324/395

[56] References Cited

U.S. PATENT DOCUMENTS 3,517,247 6/1970 Szilagyi ............ 324/395
3,978,720 9/1976 Ford ............ 324/395

*Primary Examiner*—Lee S. Cohen
*Assistant Examiner*—Marianne Harley

[57] ABSTRACT

A lithotripter is provided with the usual open ended reflector covered by a diaphragm and filled with a conductive liquid such as salinated water. A spark gap is provided at the focus point of the reflector, and a spark generator is connected thereto for providing a succession of sparks across the spark gap, wherein the light guide has an entering end positioned within the reflector and adjacent the spark gap to convey a representation of the spark outside of said reflector. The light guide has an exit end to which a light sensitive device is connected for converting the light signal to an electric signal. The electric signal is connected to means for providing a visual display of the electric signal.

10 Claims, 1 Drawing Sheet

ELECTRODE WITH VISIBLE SPARK

BACKGROUND OF THE INVENTION

Lithotripters for extracorporeal disintegration of kidney stones are now well known, and are a welcome alternative to the surgery often previously needed for excision of kidney stones. Lithotripters generally comprise a truncated ellipsoidal reflector. An ellipsoid is a geometric body of revolution having two focus points. The reflector is truncated so that the second focus point lies a few inches from the physical end of the reflector. A rubber or the like diaphragm covers the otherwise open, truncated end of the reflector, and extends somewhat beyond that end. The reflector is filled with water. A spark gap is located at the first focus point which lies within the reflector. The reflector is positioned relative to a human body so that the second focus point lies on the kidney stone to be disintegrated. High voltage sparks pass between the electrodes and set up a shockwave. The shockwave is reflected and focused by the walls of the reflector, so that the shockwaves eventually coincide at the second focus point, and in due course reduce the kidney stone to a pile of small fragments that pass out with the urine.

The voltage that causes the sparks to jump across the gap is on the order of 12,000 to 20,000 volts. A typical treatment lasts from 40 minutes to one hour, and during that time the electrodes are essentially destroyed. As the electrodes wear down the gap between them increases somewhat, and the spark begins to deteriorate after a time, and with the deterioration of the spark the shockwaves also deteriorate, thereby rendering kidney stone disintegration less efficient. It is time-consuming and expensive to have to replace electrodes during a treatment, and yet this must from time to time be done.

Heretofore, it is has not been possible to accurately access the deterioration of the electrodes in a lithotripter, and therefore it has not been possible to determine at what point the electrodes should be replaced. This leads either to too frequent replacement of electrodes to be on the safe side, or alternatively, may lead to use of a pair of electrodes long after they have ceased to produce an efficient spark and resulting shockwave.

OBJECTS AND SUMMARY OF THE PRESENT INVENTION

It is an object of the present invention to provide structure ancillary a pair of electrodes in a lithotripter for providing an indication of the efficiency of the spark produced between such electrodes.

More particularly, it is an object of the present invention to provide a unit comprising a pair of electrodes for a lithotripter, and further including fiber optics for providing a view of the spark produced between the electrodes.

It is known to provide an electrode unit comprising a pair of electrodes, an insulating base member holding the electrodes in position relative to one another, and releasable electrical connections. One such satisfactory known electrode unit is shown in our prior U.S. Pat. No. 5,047,685. The present invention comprises an improvement over that patent in that we have provided in the electrode unit a plastic fiber optic or light guide having one end adjacent the electrode gap, and the other end exiting from the insulating body to allow observation of the quality and intensity of the spark. Direct, manual observation could be made, but we prefer to use the electrode unit in combination with a light sensitive element, photocell, etc. connected to an oscilloscope to allow objective observation of the intensity and quantity of the spark.

THE DRAWINGS

The present invention will best be understood with reference to the following specification when read in accompaniment with the drawings wherein.

DETAILED DISCLOSURE OF THE ILLUSTRATED EMBODIMENT

Figure 1:
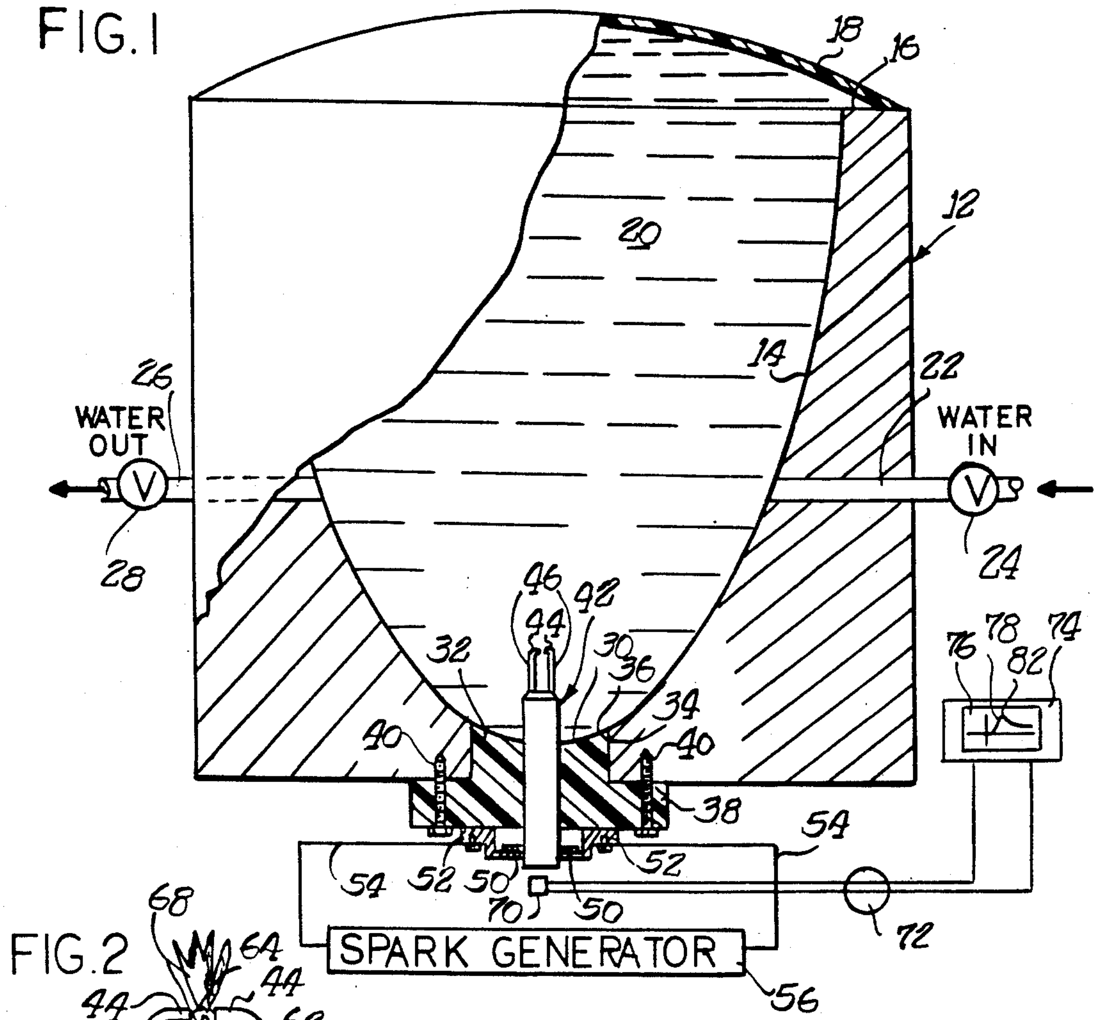
FIG. 1 is a longitudinal section through a lithotripter embodying the electrode unit of the present invention.
Figure 2:
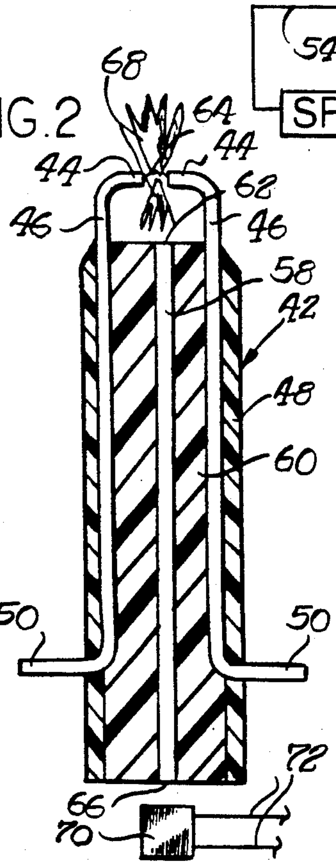
FIG. 2 is a longitudinal section through the electrode unit.

A lithotripter reflector housing 12 is generally made of brass or the like, and includes an ellipsoidal reflector 14 thereof which is truncated at an upper surface at 16. A diaphragm 18 of rubber or the like lies across the open upper end of the reflector. No specific structure is shown for securing the diaphragm, since such structures are known in the art, and may, for example comprise a band wrapped around a portion of the diaphragm depending beyond the outer edge of the trucating surface 16. The reflector is filled with water, generally saline 20. An inlet pipe 22 is provided with a valve 24 for conducting water into the reflector, and water passes out through a line 26 having a valve 28. The water thus may be replaced as necessary, and a positive pressure maintained thereon to cause the diaphragm 18 to bulge up as shown.

At the apex 30 of reflecting surface a plastic element 32 is inserted through a bore 34 in the bottom of the reflector structure 12, having an upper surface at 36 continuing the ellipsoidal reflector surface. The plastic member 32 is made of an insulating plastic resin material, and includes a peripheral flange 38 through which bolts 40 pass and are threaded into the reflector structure 12 to secure insulating insertion in place.

Figure 3:
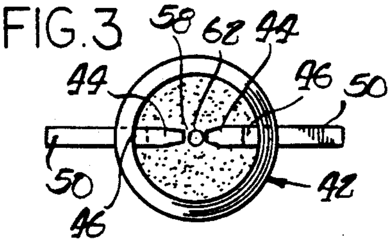
FIG. 3 is a top end view of the electrode unit.

The foregoing is generally in accordance with our previously mentioned U.S Pat. No. 5,047,685. An electrode unit 42 very similar to that in the above noted patent includes a pair of confronting tips 44 of a pair of electrodes 46. An electrode unit 42 further includes an outer cylindrical insulating shell 48 with the electrodes mounted just inside the shell and extending almost the length thereof, having outer portions 50 which are integral and which cooperate with contact structure 52, respectively, the contact structure 52 being respectively connected by wires 54 to a spark generator 56. The electrode structure or unit 42 further includes a fiber optic or light guide device 58 lying on the axis of the tube 48. A cast resinous plastic material, preferably epoxy resin 60, fills the shell 48 and holds the electrodes 46 and the fiber optic or light guide device 58 in place. The upper end 62 of the light guide is exposed at the upper surface of the cast plastic material 60 and is aligned with the gap 64 between the electrode tips 44 to view the gap. The lower end 66 of the light guide is also exposed at the lower surface of the cast plastic material 60. As best may be seen in FIG. 3 the light guide is cylindrical in nature, while the electrodes 46 are substantially square, including the outwardly directed contact portions 50 and the confronting tips 44.

Although the lower end of the light guide 58 could be viewed directly or by a mirror to ascertain whether the electrodes are producing a spark indicated at 68, it is preferred to provide a light sensitive element 70 such as a photocell aligned with the lower end 66 of the light guide, and supported in a suitable manner. The light sensitive element is connected by a pair of wires 72 to an oscilloscope 74 having a viewing screen 76 therein.

Figure 4:
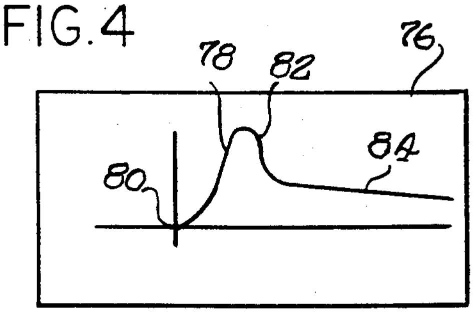
FIG. 4 is a view of the spark representation on the oscilloscope screen.

Each time a spark is produced across the confronting ends 44 of the electrodes, the light therefrom passes through the light guide to the light sensitive element 70, and a curve 78 appears on the screen 76 of the oscilloscope 74. As will be seen in FIG. 4 the curve 78 normally starts at a zero position 80, and rises rapidly to a curved peak 82, and then falls off rapidly, and finally asymptotically. The maximum amplitude of the curve 78 and the duration thereof for a good spark are established empirically. Proper coordinates can be marked on the screen 76, or a representation of the curve may be formed thereon for comparison with the curve produced during operation. In due course following a series of sparks the confronting tip surfaces 64 of the tips 44 erode, and the gap increases. The electrical conductivity may decrease, due both to the increasing gap and to corrosion of the metal at the confronting tips 64. As a result the spark curve 78 may reduce in amplitude and in duration, or it may be entirely absent. This can readily be observed on the screen 76, and an informed decision can be made from time to time whether to continue the production of sparks and shockwave with the electrode unit used at the start of the treatment, or whether the electrode unit must be replaced. This gives a far more accurate basis for a decision to replace the electrode unit than is possible with existing structure wherein all that can be told is the sound of the shockwave generated by the spark may skip occasionally, indicating that the electrodes are wearing down and not functioning properly. However, this does not give a very accurate indication of the condition of the electrodes, and it may be difficult to hear each shockwave impact in any event.

It is preferred that the saline content of the water be maintained at a constant, so as not to require interpretation of the spark curve as it might be varied with varying salinity. In any event, it can be told from observing the spark curve what the quality of the spark is. The discharge current can be measured indirectly, and missed sparks can be readily detected. Thus, an informed decision can be made as to the necessity of installing a new electrode unit. The provision of the light guide, preferably plastic fiber optic, the light sensitive element, and the oscilloscope does not add appreciably to the overall cost, and adds extremely little to the cost of the replaceable electrode unit.

The specific example of the invention as herein shown and described will be understood as being for exemplary purposes. Various changes will no doubt occur to those skilled in the art, and will be understood as forming a part of the present invention insofar as they fall within the spirit and scope of the appended claims.

The invention is claimed as follows:

1. A lithotripter comprising a reflector with an open end covered by a flexible diaphragm and having a focus point and a conductive liquid therein, an electrode unit including an insulating body having a portion within said reflector and another portion outside thereof and having a pair of electrically conducting electrodes supported by said insulating body and having confronting end portions defining a spark gap substantially at said focus point, conductive connections extending from said electrodes to a position outside said reflector, means for generating a succession of sparks connected to said conductive connections, the improvement comprising means extending through said insulating body and exposed to said spark gap for carrying a representation of a spark across said gap to a position outside said reflector, said extending means including optical means for observing said representation of a spark aimed at said spark gap.

2. A lithotripter as set forth in claim 1 wherein the extending means comprises a light guide.

3. A lithotripter as set forth in claim 2 wherein said light guide has an exit end, and light sensitive means positioned adjacent said light guide exit end for converting light from a spark to an electrical signal representing such a spark, and means connected to said converting means and including a display screen for visual display of both the magnitude and shape of the electrical signal.

4. A lithotripter as set forth in claim 2 wherein said light guide comprises a fiber optic device.

5. Apparatus comprising a body having a cavity therein, means extending from outside said body into said cavity and providing a spark gap within said cavity, means connected to said last mentioned means for providing a spark, across said spark gap, and means within said cavity facing and exposed to said spark gap and extending outside of said body for carrying a representation of a spark across said gap to a position outside said body.

6. Apparatus as set forth in claim 5 wherein said means for carrying a representation of a spark across said gap to a position outside said reflector comprises a light guide.

7. Apparatus as set forth in claim 6 wherein said light guide has an exit end, light sensitive means positioned adjacent said light guide exit end for converting light from said spark to an electrical signal representing said spark, and means connected to said converting means and including a display screen for visual display of both the magnitude and shape of the electrical signal.

8. Apparatus as set forth in claim 6 wherein said light guide comprises a fiber optic device.

9. An electrode with a visible spark comprising an elongated substantially cylindrical insulating body having a first end and a second end, a pair of electrodes extending substantially the length of said insulating body and having confronting tips disposed adjacent said first end in spaced relation thereto and defining a spark gap, said electrodes having connectors extending from said body adjacent said second end, and a light path extending substantially the length of said insulating body and having a first end substantially at said insulating body first end in optical alignment with said spark gap and having a second end externally of said insulating body adjacent said insulating body second end for observation of a spark across said spark gap.

10. An electrode as set forth in claim 9 wherein said light path comprises a fiber optic device.

* * * * *